United States Patent [19]

Teoh

[11] Patent Number: 5,288,291
[45] Date of Patent: Feb. 22, 1994

[54] METHOD AND APPARATUS FOR SIMULTANEOUSLY INJECTING A LIQUID AND A TRANSPONDER INTO AN ANIMAL

[75] Inventor: Phillip Teoh, Daly City, Calif.

[73] Assignee: Datapet, Inc., Danville, Calif.

[21] Appl. No.: 929,653

[22] Filed: Aug. 12, 1992

[51] Int. Cl.$^5$ .............................................. A61M 5/00
[52] U.S. Cl. ......................................... 604/60; 604/59; 604/218
[58] Field of Search ................ 606/116, 117; 604/57, 604/59-61, 158, 164, 170, 187, 218, 239

[56] References Cited

U.S. PATENT DOCUMENTS

| | | | |
|---|---|---|---|
| 1,325,699 | 12/1919 | Osterhaus | 604/59 |
| 3,313,301 | 4/1967 | Jefferts et al. | 606/117 |
| 4,086,914 | 5/1978 | Moore | 604/67 |
| 4,464,171 | 8/1984 | Garwin | 604/170 |
| 4,787,384 | 11/1988 | Campbell et al. | 604/60 |
| 4,828,547 | 5/1989 | Sahi et al. | 604/164 |
| 4,834,704 | 5/1989 | Reinicke | 604/891.1 |
| 4,936,827 | 6/1990 | Grimm et al. | 604/60 |
| 4,950,234 | 8/1990 | Fujioka et al. | 604/60 |

FOREIGN PATENT DOCUMENTS

| | | | |
|---|---|---|---|
| 364044 | 4/1990 | European Pat. Off. | 606/117 |
| 447623 | 3/1950 | Italy | 604/239 |
| 8901858 | 2/1991 | Netherlands | |

*Primary Examiner*—Ralph Lewis
*Attorney, Agent, or Firm*—Townsend and Townsend Khourie and Crew

[57] ABSTRACT

A method and apparatus is disclosed for simultaneously injecting medication or vaccination fluid into animal tissue and permanently placing an electronic transponder therein. An ejector is formed by a hub, which is adapted to be secured to the syringe, and from which a sharpened, hollow needle projects. Inside the needle is an elongated rod which extends into the syringe so that actuation of the syringe plunger to flow liquid through the needle forces the rod towards the sharp end of the needle. The transponder is disposed proximate the sharp end of the needle so that the rod mechanically forces the transponder with the liquid into the tissue. A sleeve which engages the rod is disposed inside an enlarged chamber defined by the hub and can move a limited extent only over the length of the rod so that the transponder can be forced into the tissue while the rod is prevented from falling out of the needle in either direction. An annular ring maintains the portion of the rod in the enlarged chamber of the hub substantially concentric with the hollow needle.

21 Claims, 2 Drawing Sheets

METHOD AND APPARATUS FOR SIMULTANEOUSLY INJECTING A LIQUID AND A TRANSPONDER INTO AN ANIMAL

BACKGROUND OF THE INVENTION

For a long time it has been necessary to positively identify animals. Historically, this was done by branding them. More recently, animal identification has made use of the versatility attained from electronic identification. For example, U.S. Pat. No. 4,787,384 discloses an apparatus for implanting a marker in an animal. The apparatus employs a sharpened needle into which the marker is placed. The needle is secured to a holder with a reciprocable rod which can be forced into the rear end of the needle, after its sharp end has been inserted into the tissue of an animal, to thereby eject the marker from the needle into the tissue. Once ejected, the needle is retracted, the incision in the animal skin is permitted to heal, and the marker is permanently located beneath the animal's skin.

Typically, the markers are electronic markers such as disclosed, for example, in U.S. Pat. Nos. 4,730,188 and 5,041,826. Briefly, the markers disclosed in these patents are passive integrated transponders disposed or embedded in a glass, plastic or the like, closed tube. Once implanted, the transponder can be excited by inductive coupling from an interrogator held or positioned on the exterior of the animal in the general vicinity of the transponder in its tissue. The transponder responds to the interrogator via the inductive coupling with a signal constituting a stream of data unique to the transponder in question. Typically, the signal is in the form of two different frequencies, a shift from one frequency to the second during a bit cell representing a data "one", and a shift from the second frequency to the first frequency representing a data "zero". The responsive signal is then detected and processed for utilization in a data storage and/or display device.

The information carried by the transponder can vary widely and as required. Typically, it will include information such as identification numbers, owner's name, address, telephone and license numbers, age and/or name of the animal, etc.

The disclosure of U.S. Pat. Nos. 4,730,188 and 5,041,826 are herewith incorporated by reference.

Prior art transponder insertion devices, such as the one described in the above-referenced '384 patent, satisfactorily position the transponder in the animal's tissue beneath its skin. However, the puncturing of the skin and the insertion and withdrawal of the needle leaves a wound. This involves discomfort for the animal and can lead to subsequent infections. Moreover, at the time the transponder is implanted, the veterinarian frequently also administers medication to reduce pain, forestall infections, or simply because the animal has been brought to him, and he, as well as the owner of the animal, prefers to take advantage of the visit to simultaneously administer medicines, vaccines, etc. This applies in particular to domestic pets such as cats and dogs, whose owners prefer to limit the number of veterinary visits they need to make with their pets.

In view thereof, it would simplify the transponder insertion procedure, would benefit the animal, and would be to the financial advantage of the animal's owner if the transponder and the vaccine could all be injected into the animal tissue simultaneously.

SUMMARY OF THE INVENTION

The present invention provides an apparatus for simultaneously injecting a liquid; e.g. medication or a vaccine, and placing a transponder into the tissue of an animal. This is achieved by placing the transponder into a sharp-ended needle attached to a veterinary syringe, conventionally operating the plunger of the syringe after the sharpened end of the needle has been inserted into the animal's tissue, to inject the medication or vaccine (hereinafter usually referred to as "liquid"). Further, the syringe plunger is mechanically coupled with the transponder in the needle by means of an elongated rod which is disposed inside the needle and has one end in contact with the transponder and the other with the syringe plunger, so that movement of the plunger to expel the liquid simultaneously ejects the transponder from the needle and thereby inserts it in the tissue.

In accordance with the present invention, this is achieved by applying an ejector to the discharge or distal end of the syringe. The syringe itself has a housing and a plunger reciprocably disposed therein, as is conventional.

The ejector of the present invention is formed by a tubular hub which has a first, proximate end for connection to the discharge end of the syringe. The hollow needle projects from the second, or distal end of the hub and has a sharp end for making an incision in the skin of the animal before the needle is advanced into the underlying tissue.

The hub has a preferably cylindrically shaped chamber the proximate end of which is defined by the discharge end of the syringe, and the distal end is defined by the proximate end of the needle; i.e. the end opposite the sharp end thereof. A rod of sufficient length is disposed inside the needle so that one of its ends is in contact with the transponder, while the other end is in contact with the plunger.

Thus, to administer a shot and implant the transponder, the plunger is manually pushed towards the discharge end of the syringe. This expels the liquid through the discharge end, the chamber and the hollow needle into the animal's tissue. Since the rod forms a mechanical connection between the plunger and the transponder, the movement of the plunger simultaneously and positively ejects the transponder from the needle and thereby inserts or implants it in the animal tissue.

To effect the simultaneous discharge of the liquid and ejection of the transponder, the rod connecting the plunger with the transponder has a lesser diameter than the inside diameter of the needle. Further, to prevent the rod from falling out of the needle when the syringe is in a generally vertical orientation; e.g. immediately before administering the shot, axial movement of the rod in the needle is limited so that the rod can neither drop rearwardly, into the housing of the syringe (which would make it difficult or impossible to thereafter actuate the plunger because the rod may not be in the proper position for reentering the needle), or forwardly, out of the needle; e.g. after the shot has been administered and the transponder has been implanted. In the preferred embodiment of the invention, this is accomplished by placing a sleeve constructed of a resilient material over the rod so that the sleeve frictionally engages the rod and can slide longitudinally along the rod when a sufficient force is applied to it, locating the sleeve inside the chamber, so that it can not enter the syringe through the discharge opening thereof or the needle through the proximate end thereof, and limiting the extent to which the sleeve can move longitudinally along the rod.

Since the rod has a lesser diameter than the interior of the needle and projects past the needle through the discharge end of the syringe, which may have a significantly larger diameter than the needle diameter, it can tilt relative to the axis of the needle. If it does tilt, the end of the rod which engages the transponder can contact the transponder eccentrically, that is not in alignment with the axis of the transponder and the needle, which can lead to jamming and/or tilt the transponder as it leaves the sharp needle end during its ejection. This can cause pain in the animal, enlarge the wound, and might even cause damage to the transponder. To prevent such tilting of the rod, a centering ring is placed inside the cylindrical chamber of the hub. The ring maintains the portion of the rod projecting from the proximal end of the needle concentric with the needle. The ring is further constructed so that it permits the flow of liquid past it to effect the desired simultaneous administration of a shot and implantation of the transponder.

As the foregoing demonstrates, the present invention makes it possible to insert the transponder and administer the liquid with one and the same instrument in one operation, requiring only one incision. This not only minimizes animal pain and the veterinarian's work, thereby also reducing overall cost, but it has the further advantage that the transponder effectively "floats" in and with the liquid into the tissue. Potentially pain-causing friction encountered when the transponder is injected dry, as is the case with the injector disclosed in the above-referenced '384 U.S. patent, is thereby eliminated.

A further significant advantage of the present invention is that it uses an ejector which does not require a separate injection device, as is the case, for example, with the injection gun disclosed in the '384 U.S. patent. Instead, the ejector of the present invention is constructed so that it can be applied to a conventional 3cc. Veterinary syringe. Such syringes are widely available at low cost and need to be used in any event when a shot is to be administered. The hub of the present invention is preferably furnished in two configurations, one with a taper (push-on) lock, and the other with a threaded lock for use with syringes having one or the other type of needle-hub connection.

A further advantage of the present invention is that the ejector of the present invention, in combination with the syringe, does not require the presence of liquid in the syringe for inserting the transponder in the animal's tissue; i.e. the transponder can be inserted by operating the hub of the syringe dry. Thus, with the present invention, the veterinarian has the same options as he had in the past; that is, he can independently administer shots and insert transponders. However, he has the desirable option of doing both simultaneously. This option is achieved without the heretofore necessary, substantial expenditures for the necessary equipment to only insert the transponder. The present invention, therefore, also offers significant cost savings to the veterinarian and ultimately to the animal owner.

DETAILED DESCRIPTION OF THE PREFERRED EMBODIMENTS

Figure 1A:
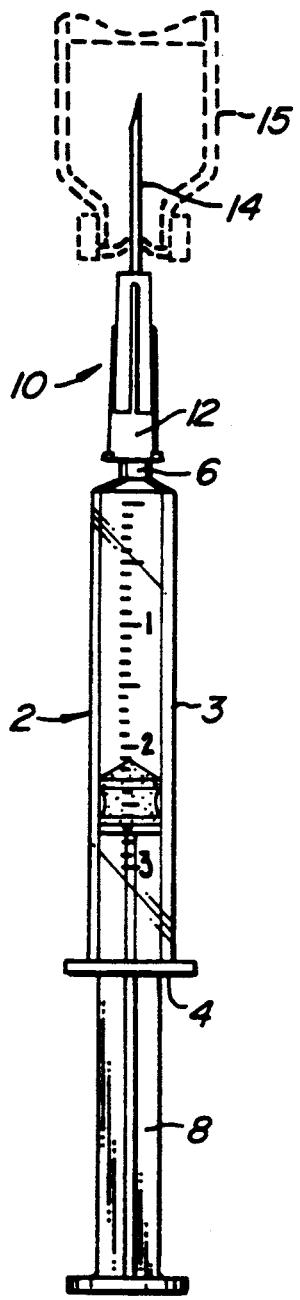
FIG. 1A illustrates a conventional syringe in position to draw a liquid such as vaccine from a vaccine-holding vial into the syringe.

FIG. 1A shows a conventional, 3cc. syringe 2 which has a housing 3 with an open end 4 and a discharge end 6. A plunger 8 is reciprocably disposed inside the housing and protrudes from the open end thereof. A conventional needle assembly 10 comprises a hub 12 and a needle (typically a #20, #21 or #25 size needle) which extends from the hub. The syringe is shown drawing a liquid; e.g. a vaccine, from a vial 16 (illustrated in broken lines) by first inserting the needle through a closing membrane in the vial into the vial and, thereafter, while the syringe is in its upright position, retracting plunger 8 relative to the housing to thereby draw the vaccine from the vial into the interior of the housing. Once the desired volume of vaccine is in the syringe, the needle is pulled out of the vial.

Figure 1B:
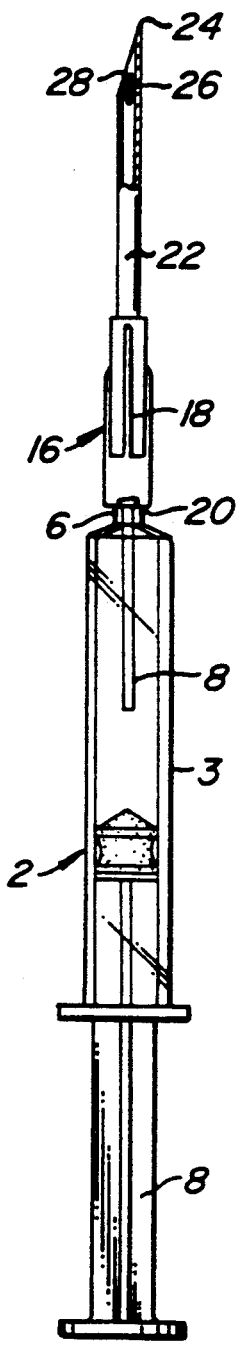
FIG. 1B illustrates the same syringe as is shown in FIG. 1A but fitted with an ejector constructed in accordance with the present invention for simultaneously administering the vaccine and inserting a transponder into the animal tissue.
Figure 2A:
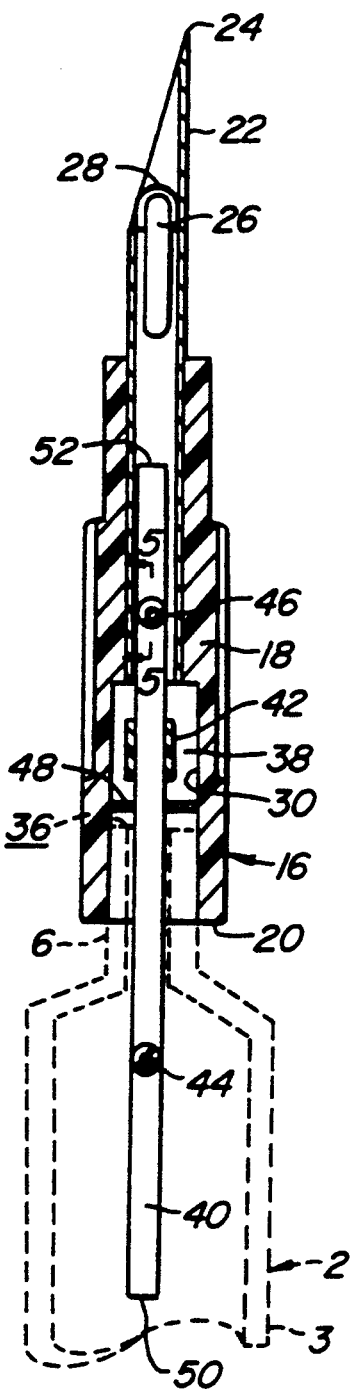
FIG. 2A is an enlarged view, in section, of the ejector of the present invention with the parts positioned as they would be immediately prior to ejecting the transponder from the needle of the ejector.
Figure 2B:
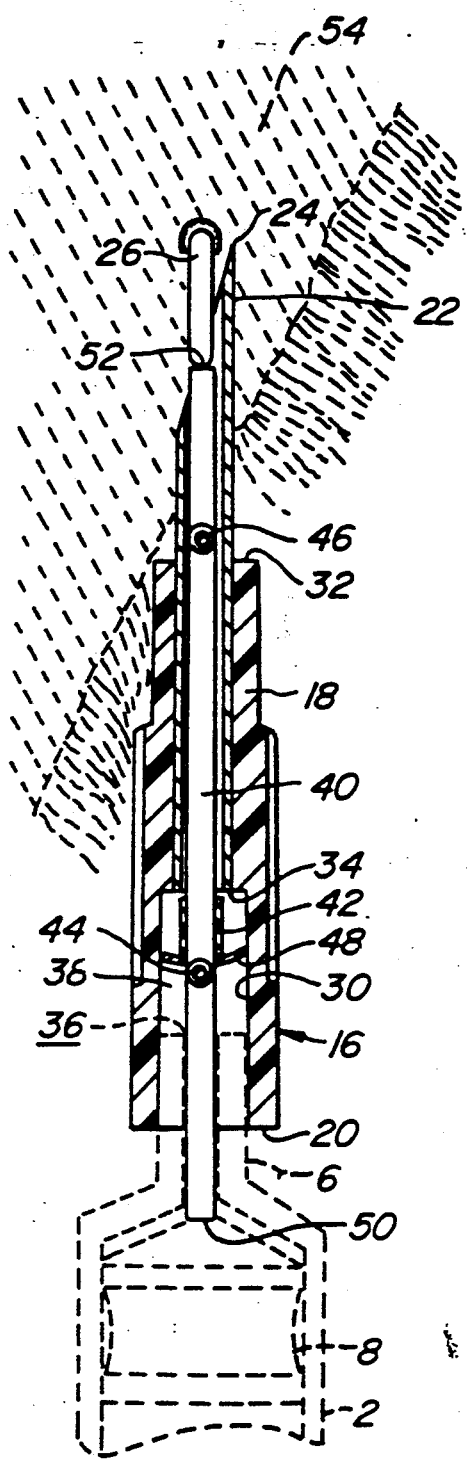
FIG. 2B is a cross-sectional view similar to FIG. 2A and illustrates the manner in which the transponder, and the vaccine, are ejected from the needle.
Figure 3:
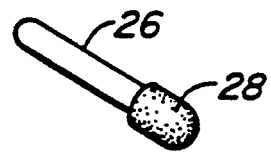
FIG. 3 is a perspective, side elevational view of a transponder fitted with an anti-migration cap.

Following the filling of the syringe with vaccine, the needle assembly 10 is removed from the discharge end and replaced with an ejector 16, shown in FIGS. 1B, 2A and 2B, constructed in accordance with the present invention. The ejector also includes a hub 18 having a proximate end 20 constructed identical to that on hub 12 shown in FIG. 1A, so that the hub can be secured to the discharge end 6 of the syringe. A relatively large-diameter needle 22, typically a #12 needle size, projects from hub 18, has a sharp, pointed end 24, and holds, adjacent the sharp end, a transponder 26. The transponder may, for example, be constructed in accordance with the above-referenced U.S. Pat. Nos. 4,730,188 and/or 5,041,826. Generally speaking, the transponder is tubular, elongated, has closed ends and, on its inside, houses the required elements for responding to an inductively coupled interrogator, for example. The detailed construction and operation of the transponder forms no part of this invention and, therefore, is not further described herein. The transponder may be fitted with an antimigration cap 28 to promote fibrous ingrowth after it has been placed into intimate contact with living tissue and, thereby, prevent the transponder from migrating inside the animal to locations different from where it was originally inserted.

The needle has a size to provide clearance between the transponder and the inside diameter of the needle so that fluid can pass therebetween. In FIG. 2A, the antimigration cap is illustrated as contacting the inside of the needle. Typically, however, the contact, if any, will be slight so that some liquid can usually pass between the cap and the needle as well.

If the transponder is to be implanted without simultaneously injecting a fluid, the needle is used "dry". In such a case, the plunger of the syringe is retracted; say, to between about the 1cc. to 2cc. marking on the syringe, and ejector 16 is applied to the discharge end thereof. From here on, the use of the syringe is as will be described below. The only difference is that at the end of the process the transponder will have been inserted in the animal tissue without the simultaneous injection of liquid. The following description of the invention assumes that liquid will be injected as well. It should be understood, however, that this would not be the case when a transponder is injected "dry".

Referring now to FIGS. 2A and 2B, ejector 16 of the present invention is preferably injection molded of a suitable plastic material, is tubular, and has a relatively large-diameter bore 30 extending from its proximal end 20 towards its distal end 32. An ejector needle 22 is suitably secured to the hub; e.g. bonded thereto or molded into it, projects from the distal end of the hub, and has an inner or proximal end 34 which coincides with the end of enlarged bore 30 or extends some distance into the bore (not shown in the drawings). The enlarged diameter bore, at least in the vicinity of proximate hub end 20, includes a taper which matches a corresponding taper on syringe discharge end 6, so that the hub can be removably secured to the syringe with a taper lock. Alternatively, for syringes having an external thread on discharge end 6, the enlarged diameter bore 30 includes a corresponding internal thread so that the hub can be threadably secured to the syringe. Syringes with either one of the connector type are widely available in the marketplace.

When the hub is secured to syringe discharge end 6, an end face 36 of the discharge end, the inner end 34 of the needle 22, and bore 30 define an enlarged diameter chamber 38.

Figure 5:
FIG. 5 is an enlarged cross-sectional view of a radial projection formed on a transponder expelling rod used with the ejector of the present invention.

Ejector 16 is further provided with an elongated rod 40 which is of a lesser diameter than the inside diameter of needle 22 and which extends from the needle rearwardly through chamber 38, the passage in syringe discharge end 6 and into the interior of the syringe housing 3. A sleeve 42, constructed of an elastomeric material, surrounds and frictionally engages rod 40 and is disposed in chamber 38. The rod includes two longitudinally spaced-apart projections 44, 46. The projections extend radially beyond the periphery of the rod so that longitudinal movement of sleeve 42 along the rod is limited to the length of rod between the two projections. In the presently preferred embodiment of the invention, the projections are formed by constructing the rod of a plastic material and inserting a heated pin or the like (not shown in the drawings) into the rod periphery so that rod material surrounding the pin wells up and thereby forms the projections, as is illustrated in FIG. 5.

Further, a washer-like, annular centering ring 48 is disposed in chamber 38. It has a diameter slightly larger than the diameter of large-diameter bore 30 and a central hole through which rod 40 extends. The hole is about the same as or only slightly larger than the outside diameter of the rod, so that the rod can pass therethrough while it maintains the portion of the rod extending through chamber 38 in substantial concentric alignment with the needle. This provides a two-fold advantage. First, it effectively prevents the end of the rod proximate sharp needle end 24 from wandering too far off center. This facilitates the ejection of the transponder in alignment with the axis of the needle. Second, the centering ring maintains the opposite end of the rod concentric with the bore 30, which facilitates the placement of ejector 16 onto syringe discharge end 6.

Figure 4:
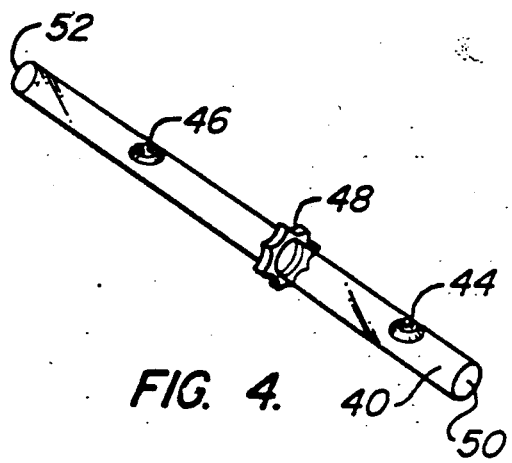
FIG. 4 is a perspective, side elevational view of a rod, including a centering device therefor, which forms part of the ejector illustrated in FIGS. 2A and 2B.

To facilitate the passage of liquid past centering ring 48, the periphery of the centering ring may be scalloped or star-shaped, as illustrated in FIG. 4, to reduce back pressure in the syringe and enable the liquid to readily flow past the ring. Typically, however, a centering ring with an only slightly larger hole through which rod 40 extends will be sufficient for the desired liquid flow past it.

Turning now to the use and operation of ejector 16, a sleeve 42 is slipped over one of the rod ends and positioned intermediate radial projections 44 and 46. A centering ring 48 is slipped over the proximate end 50 of the rod, and the distal end 52 of the rod is then inserted through bore 30 into needle 22. Centering ring 48 is pushed into bore 30 as well, and since its outer diameter is slightly larger than the diameter of the bore, it will stay frictionally engaged with the bore so that the sleeve is between the centering ring and inner needle end 34. Since sleeve 42 has an outer diameter at least equal to and preferably slightly larger than the inner diameter of the needle, and since the sleeve further frictionally engages the rod, the rod cannot slide through the needle and out of its sharpened end 24 under the influence of gravity; i.e. when the ejector is held vertically with the sharp needle end pointing downwardly. Similarly, the engagement of the sleeve by centering ring 48 prevents the rod from sliding out of the needle under the influence of gravity in the opposite direction.

A transponder 26, with or without an antimigration cap 28, can now be placed inside the needle proximate its sharp end, as is illustrated in FIG. 2A.

Assuming that the user has previously filled the syringe with a liquid, as earlier described, the ejector is now secured to the discharge end 6 of the needle so that the proximal end 50 of the rod extends into the interior of the syringe, as illustrated in FIG. 2.

Note should be taken that the length of the needle, chamber 38, syringe discharge end 6 and transponder 26 are interrelated as follows. With the transponder disposed in the needle proximate the sharp end thereof, the rod must have a length so that it extends a sufficient distance into the syringe to ensure that when plunger 8 extends the maximum distance into the syringe, it has pushed the rod towards the sharp needle end sufficiently to fully expel the transponder from the needle into the animal tissue 54. Assuming a standard hub configuration and length, the length of the rod will vary with the length of the needle attached to the hub. The length of the needle will typically vary according to the nature and size of the animal into which the transponder is to be placed.

Further, the distance between projections 44 and 46 on the rod, which limit axial movement of the sleeve along the rod, is selected so that during an injection the rod can be moved towards the sharp needle end 24 until the transponder has been fully discharged, while leaving some play between proximate rod projection 44, sleeve 42 and inside needle end 34. Further, the distance between the projections is selected so that the rod can be pushed rearwardly; that is, towards the syringe, a sufficient distance to enable the full insertion of the transponder into the front end of the needle while leaving play between the distal projection 46, sleeve 42 and syringe discharge end face 36.

When the rod length and the spacing between the rod projections is as above described, the rod cannot gravitationally drop rearwardly into the interior of the syringe if the syringe, with ejector 16 secured thereto, is held upright, for example, immediately before inserting the sharp needle end into the animal tissue. If the rod were permitted to drop into the syringe interior as far as permitted by the relative position of plunger 8, its distal end 52 may become disengaged from the needle interior and misaligned therewith. This would make it impossible to move the plunger forwardly to expel the liquid and the transponder from the needle; i.e. if this were permitted to happen, malfunction of the ejector would ensue.

Turning back to the use of the injector, and with the syringe holding the desired quantity of a liquid and a transponder in position proximate to the sharp needle end 24, the user aims the sharp needle end at the point on animal skin 56 where he chooses to insert the transponder. Once the incision has been made, the needle is thrust a short distance further into the tissue to prevent a backflow of vaccine out of the incision. Thereafter the plunger is conventionally forced into the syringe housing, thereby flowing the liquid through chamber 38, the annular space between the inside of needle 22 and rod 40, and hence out of the sharpened end 24 into the animal tissue. The liquid flow may move the transponder with it, especially if it includes an antimigration cap 28, until the transponder encounters the tissue and increased resistance against further forward movement. However, as the plunger advances into the syringe, it eventually contacts proximal rod end 50, thereby moving the rod with it. As soon as the distal rod end 52 engages the transponder, the plunger becomes mechanically coupled to the transponder. Further movement of the plunger into the syringe housing forcibly expels the plunger from the needle and thereby embeds it in the surrounding tissue. As mentioned earlier, the liquid surrounding the plunger during its ejection acts both as a lubricant and an aid for "floating" the transponder into the tissue, which makes the entire process easier to perform and less painful for the animal.

Thereafter, the syringe, with the injector, is retracted from the animal tissue and past the incision in the animal's skin. Even if the distal rod end 52 extends partially past the needle end; e.g. if it should extend into the tapered portion of the needle and, therefore, come in contact with the tissue, it cannot become lodged therein. At most, the rod will be partially pulled out of the sharp needle end, but only until one end of sleeve 42 engages inside needle end 34 and the other end engages proximal rod projection 44, because from that point on further relative movements between the rod and the needle are prevented. As a result, upon the complete retraction of the needle from the tissue the rod will also be completely retracted, permitting the incision to close and thereafter to heal.

What is claimed is:

1. An ejector for use with and adapted to be attached to a discharge end of a syringe for injecting a liquid into living tissue and simultaneously placing an object into the tissue, the ejector comprising a tubular hub adapted to be attached to a liquid discharge end of the syringe having proximal and distal ends; an elongated, hollow needle secured to the hub, projecting from the distal end and having a sharp end adapted to make an incision in the tissue, the needle terminating short of the proximal end of the hub, the hub defining a chamber between the proximal end of the needle and the proximal end of the hub which has a larger cross-section than the needle; an elongated rod reciprocable disposed in the needle, having a diameter less than the inside diameter of the needle and a sufficient length so that it extends into the syringe when the hub is attached to the syringe; and retaining means disposed in the chamber and operably coupled with the rod for preventing the rod from axially moving under the influence of gravity out of either end of the needle, the retaining means comprising a sleeve frictionally engaging the rod and, upon the application of an axial force thereto, movable along the rod; whereby the object can be placed into the needle so that the object is forced by the rod through the incision into the tissue when a plunger of the syringe is moved towards the hub for injecting the liquid and thereby engages and moves the plunger relative to the needle towards the sharp end thereof.

2. An ejector according to claim 1 wherein the sleeve is constructed of an elastomeric material.

3. An ejector according to claim 1 including stop means limiting the extent to which the sleeve is longitudinally movable relative to the rod.

4. An ejector according to claim 3 wherein the stop means comprise first and second, longitudinally spaced apart, radially oriented projections on the rod which engage and thereby limit the movement of the sleeve along the rod.

5. An ejector according to claim 4 wherein the projections comprise upwelled material of the rod.

6. An ejector according to claim 1 including means disposed in the chamber for substantially centering a portion of the rod disposed in the chamber and for permitting the passage of liquid through the chamber and past the centering means.

7. An ejector according to claim 6 wherein the centering means comprises an annular member.

8. An ejector according to claim 7 wherein the annular member engages an interior wall of the chamber, has an inner diameter for maintaining the rod portion inside the chamber substantially centered relative to the needle, and includes means permitting axial liquid flow past the annular ring.

9. An ejector according to claim 8 wherein the flow permitting means comprises radial indentations on a periphery of the annular member.

10. An ejector according to claim 8 wherein the flow permitting means comprises clearance between the rod and an inside of the annular member.

11. An ejector according to claim 1 in combination with the object, wherein the object comprises an elongated member having a diameter less than an inside diameter of the needle.

12. An ejector according to claim 11 wherein one end of the object includes a porous cap for promoting fibrous ingrowth into the cap after the object has been placed in the tissue to prevent migration of the object in the tissue.

13. An ejector for placement over a distal, open end of a syringe for administering liquid medication and adapted to simultaneously place an electronic transponder into living tissue, the ejector comprising a tubular hub having a first end for connection to the open syringe end; a hollow needle projecting from a second end of the hub and having a sharp end for entering the tissue, the hub defining a chamber which is concentric with the needle and has a diameter larger than an inside diameter of the needle; an elongated rod reciprocably disposed in the needle and having a length so that it extends from proximate the sharpened end of the needle into an interior of the syringe when the hub is secured to the syringe; a sleeve disposed in the chamber and movably engaging the rod for limiting longitudinal movements of the plunger relative to the needle so that the rod is prevented from moving under the influence of gravity out of the needle in either direction when the hub is secured to the syringe; and means limiting the extent to which the sleeve can move along the rod.

14. Apparatus for simultaneously injecting a liquid and placing an electronic transponder into living tissue, the apparatus comprising:
  a syringe having a hollow housing for holding the liquid, a liquid discharge end, and a plunger reciprocably disposed in the housing;
  a tubular hub secured to the discharge end of the housing and defining a relatively large cross-section chamber extending from the discharge end of the housing towards a distal end of the hub;
  a hollow needle projecting from the distal end of the hub and having a sharp, free end for insertion into the animal tissue;
  an elongated rod disposed inside the needle having a distal end proximate the sharp needle end, extending through the chamber, and having a proximal end disposed inside the housing so that the proximal end can be engaged by the plunger when it is moved relative to the housing towards the discharge end thereof and so that, during such movement, the plunger forcibly moves the rod towards the sharp end of the needle; and
  stop means operatively coupled with the rod for preventing movement of the rod under the influence of gravity out of the needle, the stop means including a sleeve disposed inside the chamber, in frictional engagement with the plunger and movable along a portion of the rod;
  whereby the transponder can be placed inside the needle proximate the sharp end thereof and movement of the plunger relative to the housing towards the discharge end simultaneously ejects liquid and the transponder from the sharp needle end into the animal tissue.

15. Apparatus according to claim 14 wherein the stop means further includes means limiting movement of the sleeve relative to the rod over a predetermined length of the rod intermediate the ends thereof.

16. Apparatus according to claim 14 including centering means disposed in the chamber for maintaining a portion of the rod outside of the needle in substantial alignment with the needle, the centering means including means permitting liquid to flow past it through the chamber.

17. A method for simultaneously injecting a liquid and placing an electronic transponder into live tissue comprising the steps of providing a hollow, sharp-ended needle attached to an end of a veterinary syringe including a plunger reciprocably disposed inside a syringe housing, placing the electronic transponder into the needle, and at least partially filling the housing with a liquid with the sharp needle end making an incision in the animal tissue, moving the plunger relative to the housing to force the liquid from the housing through the needle and into the tissue, and mechanically coupling the plunger with the electronic transponder so that movement of the plunger to inject the liquid from the housing simultaneously mechanically forces the electronic transponder out of the needle and into the tissue.

18. A method according to claim 17 wherein the step of mechanically coupling comprises the step of positioning an elongated rod between the plunger an the transponder so that movements of the plunger in the syringe housing are mechanically transmitted to the transponder.

19. A method according to claim 18 including the steps of retracting the needle from the tissue and constraining the rod to the needle to simultaneously retract the rod form the tissue and thereby prevent the rod from remaining in the tissue.

20. A method according to claim 18 including the step of preventing movement of the rod out of the needle under the influence of gravity. relative to the housing towards the discharge end simultaneously ejects liquid and the transponder from the sharp needle end into the animal tissue.

21. An ejector for use with and adapted to be attached to a discharge end of a syringe for injecting a liquid into animal tissue and simultaneously placing an object into the tissue, the ejector comprising a tubular hub adapted to be attached to a liquid discharge end of the syringe having proximal and distal ends; an elongated, hollow needle secured to the hub, projecting from the distal end and having a sharp end adapted to make an incision in the tissue, the needle terminating short of the proximal end of the hub, the hub defining a chamber between the proximal end of the needle and the proximal end of the hub which has a larger cross-section than the needle; an elongated rod reciprocably disposed in the needle, having a diameter less than the inside diameter of the needle and a sufficient length so that it extends into the syringe when the hub is attached to the syringe; retaining means disposed in the chamber including a sleeve movable along the rod for preventing the rod from axially moving under the influence of gravity out of either end of the needle; and stop means for limiting the extent to which the sleeve is movable along the rod and comprising first and second, longitudinally spaced-apart, radially oriented projections on the rod defined by upwelled material of the rod which engage and thereby limit the movement of the sleeve along the rod; whereby the object can be placed into the needle so that the object is forced by the rod through the incision into the tissue when a plunger of the syringe is moved towards the hub for injecting the liquid an thereby engages and moves the plunger relative to the needle towards the sharp end thereof.

* * * * *